United States Patent [19]

Ohtake et al.

[11] 4,318,618
[45] Mar. 9, 1982

[54] APPARATUS FOR AUTOMATICALLY MEASURING CHANGING VALUES OF ABSORBANCE

[75] Inventors: Yukio Ohtake; Masahiro Nakamura, both of Tokyo, Japan

[73] Assignee: Ohtake Works Company, Ltd., Tokyo, Japan

[21] Appl. No.: 126,242

[22] Filed: Mar. 3, 1980

[30] Foreign Application Priority Data

Mar. 13, 1979 [JP] Japan .................................. 54-28211

[51] Int. Cl.³ .............................................. G01N 21/01
[52] U.S. Cl. .................................................. 356/435
[58] Field of Search ................................ 356/432–442; 250/564, 565, 575

[56] References Cited

U.S. PATENT DOCUMENTS

| | | | |
|---|---|---|---|
| 2,939,361 | 7/1960 | Hock | 250/564 |
| 3,609,047 | 9/1971 | Marlow | 356/434 |
| 3,838,925 | 10/1974 | Marks | 356/438 |
| 3,982,838 | 9/1976 | Thacker | 356/440 |
| 4,208,129 | 6/1980 | Spencer | 356/435 |
| 4,234,538 | 11/1980 | Ginsberg et al. | 356/435 |
| 4,240,753 | 12/1980 | Brück | 356/442 |

FOREIGN PATENT DOCUMENTS 1183472  3/1970  United Kingdom ................ 356/432
2000284  1/1979  United Kingdom ................ 356/435

*Primary Examiner*—John K. Corbin
*Assistant Examiner*—Bruce Y. Arnold
*Attorney, Agent, or Firm*—Jordan and Hamburg

[57] ABSTRACT

Apparatus for automatically measuring changing values of absorbance comprise a circular, absorption cell conveying system on which are disposed in order a multitude of absorption cells with samples injected therein, an optical measurement system disposed so that a measuring zone is positioned therewithin, said measuring zone is disposed in a predetermined position of said absorption cell conveying system, a measurement conversion system for encoding a measured value signal output from said optical measurement system with respect to each said absorption cell conducted successively into said measuring zone, a reference conversion system for encoding a reference value signal output from said optical measurement system, a synchronizing command system for generating a synchronizing signal upon sensing of the arrival of each said absorption cell at said measuring zone, and an arithmetic recording system including a microcomputer for inputting in parallel the output signals respectively from said measurement conversion system, reference conversion system and synchronizing command system and calculating a value of change in absorbance of each said absorption cell.

1 Claim, 4 Drawing Figures

APPARATUS FOR AUTOMATICALLY MEASURING CHANGING VALUES OF ABSORBANCE

This invention relates to method and system for automatically measuring changing values of absorbance used for the study of monitoring with the lapse of time the activity, tissue metabolism, growth action, etc. of many enzymes contained in animals, plants and microorganisms.

Heretofore, the absorbance analysis method has generally been used for optically analyzing the metabolism and growth action of microorganisms in culture fluid. For example, a photoelectric colorimeter and a spectrophotometer have been used in both of which light is transmitted into solution within a vessel and the intensity of the transmitted light and the change in spectrum are analyzed. In these methods, however, it has been necessary before measurement to make zero setting and 100% setting of the scale of a measuring instrument or the like. In such zero setting and 100% setting, first the shutter is closed to prevent light from entering the photo detector portion and in this condition a setting is made to 100%, then a solvent or a blank test solution is charged into an absorption cell, which is put in the optical path, after which the shutter is opened and the sensitivity adjusting knob of the photo detector portion or slit is set to 0%. In such a series of operations, adjustment is repeated many times until a 100% setting is effected when the shutter is closed and a 0% setting when it is opened. This is disadvantageous in that the operation is troublesome and time-consuming and a setting error cannot be avoided. In an attempt to remedy such drawbacks there have been proposed various methods, for example, the combination of a servomotor and a potentiometer for effecting the said adjustment automatically, and the method of setting the slit width optically and automatically. In all these methods, the equipment has been large-sized and expensive.

It is an object of this invention to provide a method and system for automatically measuring changing values of absorbance which dispenses with the need for obtaining a zero setting and a 100% setting and in which a multitude of samples are measured time-division-wise, during a fixed period.

Other objects of this invention will become apparent by referring to this specification and the accompanying drawings, in which.

An embodiment of this invention is described below with reference to FIG. 1.

Figure 1:
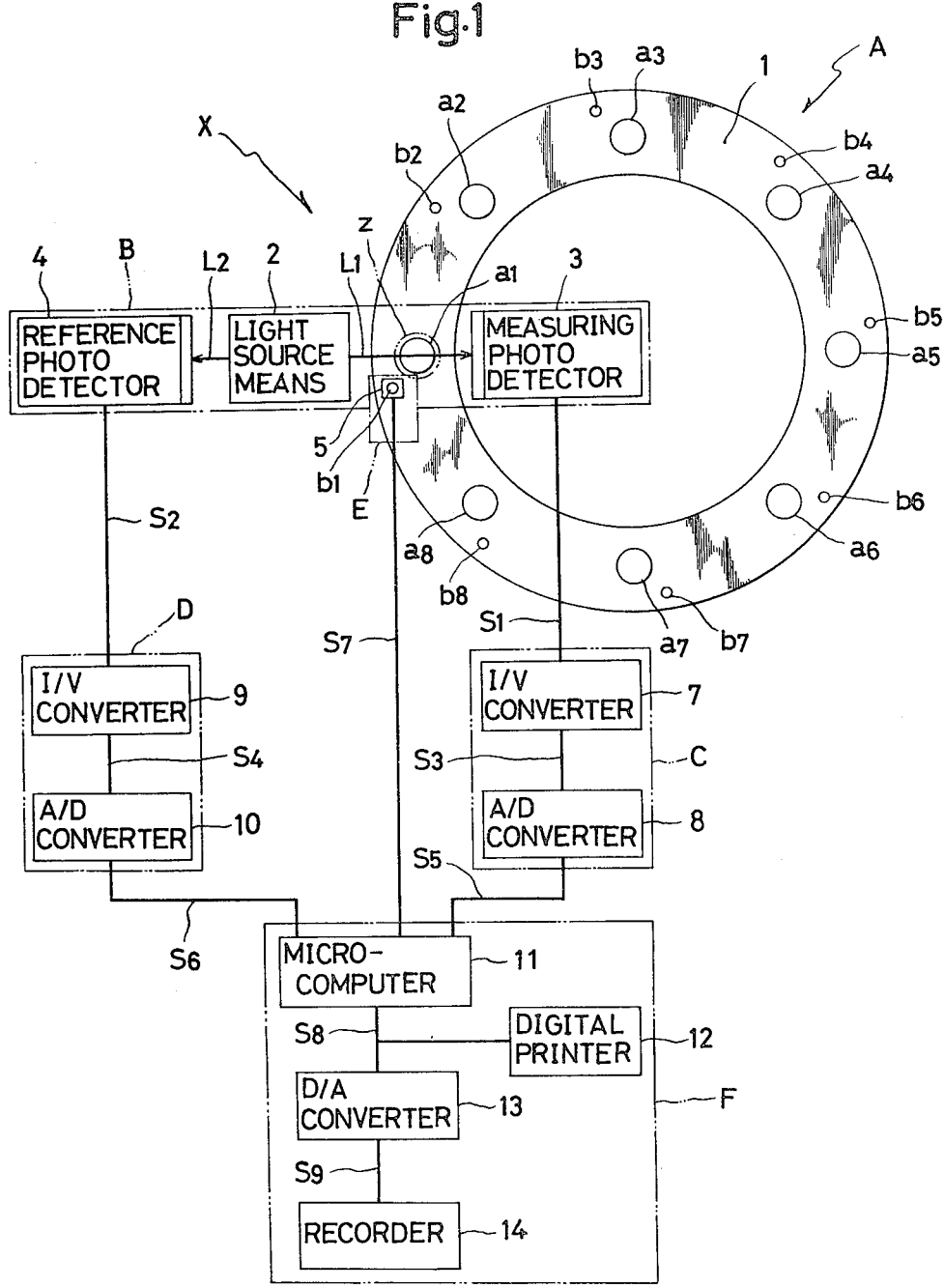
FIG. 1 is a conceptual construction diagram of a system for automatically measuring changing values of absorbance according to this invention.
Figure 2:
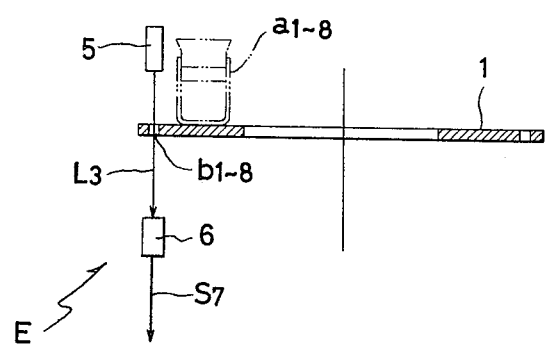
FIG. 2 illustrates the arrangement showing one embodiment of a synchronizing command system according to this invention.

As shown in FIG. 1, the system X of this invention comprises a circular, absorption cell conveying system A, an optical measurement conversion system C, a reference conversion system D, a synchronizing command system E, and an arithmetic recording system F.

Figure 3:
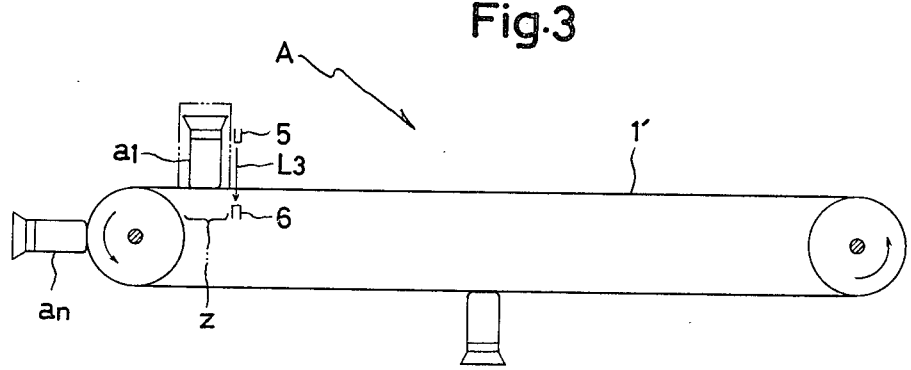
FIGS. 3 and 4 are a side view and a plan view, respectively of another circular, absorption cell conveying system in the system for automatically measuring changing values of absorbance of this invention.
Figure 4:
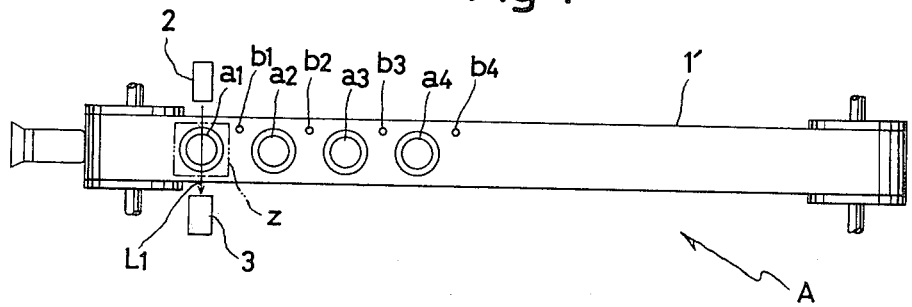

The absorption cell conveying system A includes a ring conveyor 1 which forms a plane, endless circular path on which are disposed absorption cells $a_1$–$a_8$ circumferentially at equal intervals, the absorption cells containing samples such as culture fluids, enzymes and reagents. The ring conveyor 1 is turned in a continuous travelling form or in an intermittent pitch feed form by a drive motor (not shown) to conduct the absorption cells successively into a measuring zone, z, disposed in a predetermined position whereby changes in growth action within all the absorption cells $a_1$–$a_8$ are measured at every fixed period. Furthermore, in order that the synchronizing command system E may detect the arrival of each of the absorption cells $a_1$–$a_8$ at the measuring zone, z, there are formed detection holes $b_1$–$b_8$ in the vicinity of and on the same radius as the absorption cells $a_1$–$a_8$, the detection holes $b_1$–$b_8$ being disposed circumferentially at equal intervals. The circular, absorption cell conveying system A is not limited to the ring conveyor 1 here shown; it may be a slat conveyor (not shown) which forms a side, endless circular path, or may be such a belt conveyor 1' as shown in FIGS. 3 and 4, if only it allows the absorption cells $a_1$–$a_8$ to circulate into the measuring zone, z, at a fixed period. In this case, the arrangement of the absorption cells $a_1$–$a_8$ can be set optionally.

The optical measurement system B includes light source means 2 which emits a light beam $L_1$. The light beam $L_1$ passes through the measuring zone, z, of the absorbance cell conveying system A and, to detect the transmitted light $L_1$, there is disposed by suitable means a measuring photodetector with filter 3 in opposed relation to the light source means 2, and the conveyor 1 and the measuring zone, z, are located therebetween. With the measuring photo detector with filter 3, the transmitted light $L_1$ is subjected to photoelectric conversion and a measured analog current signal, $s_1$, is output. On the other hand, there is disposed a reference photo detector with filter 4 which catches and effects photoelectric conversion of a reference light $L_2$ emitted from the light source means 2, and outputs a reference analog current signal, $s_2$.

The synchronizing command system E comprises a synchronizing light source 5 and a synchronizing photo detector 6 which are disposed in opposed relation on the same optical axis with the ring conveyor 1 put therebetween so that a detection light $L_3$ passes through the detection holes $b_1$–$b_8$ which are formed at equal intervals in the ring conveyor 1, the synchronizing photodetector 6 functioning to catch the detection light $L_3$ and effect photoelectric conversion thereof into a synchronizing signal, $s_7$.

When as the conveyor 1 rotates the detection light $L_3$ has passed one of the detection holes $b_1$–$b_8$ and been caught by the synchronizing photo detector 6, the synchronizing signal, $s_7$, resulting from photoelectric conversion by the photo detector 6 is delivered to the arithmetic recording system F, and thus the arrival of the absorption cells $a_1$–$a_8$ at the measuring zone, z, is detected.

The detection holes $b_1$–$b_8$ may be substituted by projections, and a microswitch which comes into contact successively with the said projections may be used in place of the synchronizing light source 5 and synchronizing photo detector 6. Furthermore, index pieces may be embedded in the conveyor 1 in place of the detection holes $b_1$–$b_8$, and a proximity (contactless) switch capable of detecting the index pieces successively may replace the synchronizing light source 5 and synchronizing photo detector 6.

The measurement conversion system C and the reference conversion system D comprise I/V converters 7, 9 and A/D converters 8, 10. Since the electric signals obtained from the optical measurement system B are analog current signals represented by the strength of continuous current, they must be converted into digital voltage signals before introduction into the arithmetic circuit pckaged in a microcomputer. And this conversion is effected through the I/V converters 7, 9 and the A/D converters 8, 10.

The measured analog current signal, $s_1$, from the measuring photodetector 3 in the optical measurement system B and the reference analog current signal, $s_2$, from the reference photo detector 4 in the same system go through the I/V converters 7 and 9, respectively, from which there are output a measured analog voltage signal, $s_3$, and a reference analog voltage signal, $s_4$, go through the A/D converters 8 and 10, respectively, whereby they are encoded into a measured digital voltage signal, $s_5$, and a reference digital voltage signal, $s_6$, capable of being subjected to electronic calculation.

The arithmetic recording system F is constituted by a microcomputer 11, a digital printer 12 connected thereto and a recorder 14 connected through D/A converter 13 to the microcomputer 11.

The measured digital voltage signal, $s_5$, and the reference digital voltage signal, $s_6$, from the measurement conversion system C and the reference conversion system D are introduced in an absorbance calculating circuit (not shown) packaged in the microcomputer 11 upon receipt of the synchronizing signal, $s_7$, from the synchronizing photo detector 6 or the synchronizing command system E. Then, the absorbance value is obtained according to the operational procedure of a predetermined absorbance calculating expression program-stored in advance. The initial absorbance values of the absorption cells $a_1$–$a_8$ are readably stored in memory elements in designated addresses which are in correspondence to the absorption cells $a_1$–$a_8$. Every time the next and following absorbance values are obtained by the absorbance calculating circuit at every fixed period of each of the absorption cells $a_1$–$a_8$, the aforesaid initial absorbance value is read from the memory element concerned, and the value of difference between the two is calculated by a value-of-change-in-absorbance calculating circuit according to the operational procedure of a predetermined value-of-change-in-absorbance calculating circuit program-stored in advance, and a digital value-of-change-in-absorbance signal, $s_3$, is obtained. The digital value-of-change-in-absorbance signal, $s_8$, is connected to the digital printer 12 and at the same time it is converted through the D/A converter 13 to an analog value-of-change-in-absorbance signal, $s_9$, which is recorded by the recorder 14.

Now an explanation is given as to the absorbance calculating expression and the value-of-change-in-absorbance calculating expression both program-stored in the absorbance calculating circuit and the value-of-change-in-absorbance calculating circuit of the microcomputer 11, respectively.

First as to the absorbance calculating expression used in the invention, the expression $A = \log I_o/I$ (A ... absorbance, I ... intensity of transmitted light $L_1$, $I_o$ ... intensity of reference light $L_2$) representative of the Lambert-Beer's Law as a conventional absorbance analyzing method is introduced in the absorbance calculating circuit of the microcomputer 11. Then, the measured digital voltage signal, $s_5$, and the reference digital voltage signal, $s_6$, are input to the I and $I_o$ in the above expression, respectively. In this condition, the absorbance of each of the absorption cells $a_1$–$a_8$ which are circulating on the circular conveyance path is calculated successively (if the total number of measurement is divided by the number of absorption cells, the quotient is the number of measurement of a certain absorption cell and the remainder is the order (No.) of the absorption cell). The actual calculation procedure in the absorbance calculating circuit of the absorbance calculating expression program-stored is executed according to the following steps.

i. Input of I ... input of the measured digital voltage signal, $s_5$ ii. Calculating of log I ... calculation of log $s_5$ iii. Input of $I_o$ ... input of the reference digital voltage signal, $s_6$ iv. Calculation of log $I_o$ ... calculation of log $s_6$ v. log $I_o$ − log I = A ... log $s_6$ − log $s_5$ = absorbance value Next, as to the value-of-change-in-absorbance calculating expression used in the invention, the initial absorbance value obtained after a certain absorption cells, a, has made a round is stored in a memory element of the microcomputer 11 and at every input of the synchronizing signal, $s_7$, it is read out for calculation of a value of difference from the next and following absorbance values in the value-of-change-in-absorbance calculating circuit. In this case, the expression $A'n = A_n+1 − A_1$ ($A'$ ... value of change in absorbance, A ... absorbance, n ... the number of times of data) is introduced in the value-of-change-in-absorbance calculating circuit of the microcomputer 11. That is, the first value of change in absorbance is $A'_1 = A_2 − A_1$. Substituting the foregoing expression of absorbance $A = \log I_o/I$ into the said expression gives $$A'_1 = A_2 - A_1 = (\log I_o/I_2) - (\log I_o/I_1)$$

Removing the parentheses gives $$A'_1 = \log I_o - \log I_2 - \log I_o + \log I_1$$

Thus, $$A'_1 = \log I_1 - \log I_2, \text{ with } \log I_o \text{ eliminated}$$

Thus according to the calculation method for a value of change in absorbance used in the invention, the computer 11 does not require input of the reference digital voltage signal, $s_6$, on the premise that $I_o$ is constant. Actually, however, the $I_o$ is not always constant because with the lapse of time the light source means 2 undergoes changes based on the environment and conditions, causing variations in voltage and in luminous intensity. Therefore, the reference photo detector 4 and the reference conversion system D cannot be omitted, they have the function of a compensating circuit which absorbs and corrects variations occurring with the lapse of time of the reference light $L_2$. Specially in this invention in which the operation and monitoring are performed automatically in unmanned condition for an extended period of time, such compensating function is very effective and assures measurements of high accuracy.

According to the method and system for automatically measuring changing values of absorbance of this invention described as above, light is directed to an absorption cell which circulates at every fixed period and the transmitted light is analyzed, the principle of measurement being quite the same as that of the conventional absorbance measuring technique. However, the calculation of absorbance according to this invention is to obtain a value of change in absorbance by utilization of a computer, differentiated from the conventional calculation of absorbance (absolute value) in which zero setting and 100% setting are made. Consequently, the calculation of absorbance according to the invention can dispense with such zero setting and 100% setting (the absorbance need not be an absolute value) and hence can dispense with the apparatus and implements which heretofore have been used for this purpose, so that the preparations for experiment can be completed in a short time without taking trouble in adjustment. Furthermore, a multitude of samples can be subjected to automatic measurement and calculation with the lapse of time and time-division-wise at a fixed period, and the results can be recorded by a printer, a recorder of the like. Thus, the method and system of this invention are best suited for the measurement of ever-changing growth state and tissue of microorganisms and reaction velocity of solution. Besides, if a ring conveyor which forms a plane endless circular path is used as the absorption cell conveying system, the absorption cells can be circulated in a stationary state, while if a slat conveyor or belt conveyor which forms a side endless circular path is used, the absorption cells can be shaked at the front-rear turning end. This invention provides these excellent effects.

What is claimed is:

1. Apparatus for automatically measuring changing values of absorbance in absorbance cell means comprising, conveying means moving said absorbance cell means along a fixed path and through a fixed measuring zone located along said fixed path, a light source means fixed in position at said measuring zone for emitting a non-splitting transmission light and a reference light from a common source of light, measuring photodetector means fixedly positioned at said measuring zone and optically aligned and spaced from said light source means such that said cell means, when moving along said fixed path, passes through said measuring zone between said light source means and said measuring photodetector means, said measuring zone being defined by an open space between said light source means and said measuring photodetector means such that when said cell means passes through said open space, said transmission light passes directly from said light source means through said cell means to said measuring photodetector means devoid of any other interference, said measuring photodetector means effecting a photoelectric conversion thereof into a measured value signal, a reference photodetector means optically aligned with said light source means receiving said reference light and effecting a photoelectric conversion into a reference value signal, said reference light passing directly from said light source means to said reference photodetector means devoid of any interference between said light source means and said reference photodetector means, a synchronizing command system for generating a synchronizing signal upon sensing the arrival of each cell means at said measuring zone, and operable means receiving said measuring value signal, said reference value signal and said synchronizing signal and calculating the values of absorbance of said cell means each time a cell means passes through said measuring zone, said values of absorbance being successively and accurately calculated without requiring compensation for variations of the light intensity of said light source means, said operable means comprising a measurement conversion system for encoding a measured value signal output from said measuring photodetector means with respect to each of said absorption cell means passing successively into said measuring zone, said measurement conversion system comprising an I/V converter means for converting a measured analog current signal from said measuring photodetector means into a measured analog voltage signal and an A/D converter means for encoding said measured analog voltage signal into a measured digital voltage signal, said I/V converter means and said A/D converter means being connected in series with each other, said operable means further comprising a reference conversion system for encoding a reference value signal output from said reference photodetector means, said reference conversion system comprising an I/V converter means for converting a reference analog current signal from said reference photodetector means into a reference analog voltage signal, and an A/D converter means for encoding said reference analog voltage signal into a reference digital voltage signal, the last said I/V converter means and the last said A/D converter means being connected in series with each other, said operable means further comprising an arithmetic recording system including a microcomputer means for inputting in parallel the said signals respectively from said measurement conversion system, said reference conversion system and said synchronizing command system and calculating the value of change in absorbance of each of said absorbance cell means as the latter pass through said measuring zone, said microcomputer means comprising an absorbance calculating circuit which receives, when each of said absorption cell means has arrived at said measuring zone, a synchronizing signal from said synchronizing command system, a measured value signal from said measurement conversion system with respect to each of said absorption cell means, and a reference value signal from said reference conversion system and calculates the absorbance of each of said absorbance cell means, memory elements at designated addresses corresponding to said absorption cell means, said memory elements storing readably the initial value of said absorbance of each of said absorption cell means, and a value-of-change-in-absorbance calculating circuit means for calculating the differences in absorbance values between successive absorbance values as calculated by said absorbance calculating circuit and said initial values stored in said memory elements.

* * * * *